United States Patent
Allen et al.

[11] Patent Number: 6,100,058
[45] Date of Patent: Aug. 8, 2000

[54] GAP12 GENES AND THEIR USES

[75] Inventors: Maxine J. Allen, San Diego; Alan J. Buckler, Encinitas, both of Calif.

[73] Assignee: AxyS Pharmaceuticals, Inc., South San Francisco, Calif.

[21] Appl. No.: 08/909,954

[22] Filed: Aug. 12, 1997

[51] Int. Cl.[7] .................... C12P 21/06; C07H 21/02; C07H 21/04; C12N 9/00
[52] U.S. Cl. ............... 435/69.1; 435/320.1; 435/325; 435/183; 536/23.2; 536/23.1; 530/324
[58] Field of Search .................. 536/23.1, 23.2; 435/6, 7.23, 325, 320.1, 183, 69.1; 530/324

[56] References Cited

PUBLICATIONS

EMBL–est accession number AA797574, 1996.
EMBL–est accession number AA497997, 1996.
EMBL–est accession number AA062153, 1996.
EMBL–est accession number AA203831, 1996.
Sambrook et al. Molecular Cloning: A Laboratory Manual, Cold Spring Harbor, pp. 1.53–1.74, 1990.
Taylor e tal. genbank accession No. U58012, 1996.
Ma et al. genbank accession No. U47812, 1996.
Merkle et al. genbank accession No. L16788, 1995.
Hudson et al. genbank accession No. G22228, 1996.
Stahle–Backdhal et al. (1995) *Am. J. Pathol. 146*:1073–1078.
Friedman (1995) *Pathobiology 63*:348–350.
Shen et al. (1996) J. Med. Genet. 33:2–17.
Scheffzek et al. (1996) *Nature 384:*591–596.
Ahmadian et al. (1996) *J Biol Chem 271*:16409–16415.
Genbank accession No. M89914 (1995), Xu et al.
Swissprot accession No. P20936 (1997), Trahey et al.
Genbank accession No. L33075 (1995), Weissbach L. et al.
Genbank accession No. U51903 (1996), Brill et al.
Trofatter et al. (1995) Genome Research 5:214–224.
Predergast and Gibbs (1994) BioEssays 16:187–191.

*Primary Examiner*—Yvonne Eyler
*Attorney, Agent, or Firm*—Pamela J. Sherwood; Bozicevic, Field & Francis, LLP

[57] ABSTRACT

Methods for isolating GAP12 genes are provided. The GAP12 nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as identification of cell type based on expression, and the like.

7 Claims, 1 Drawing Sheet

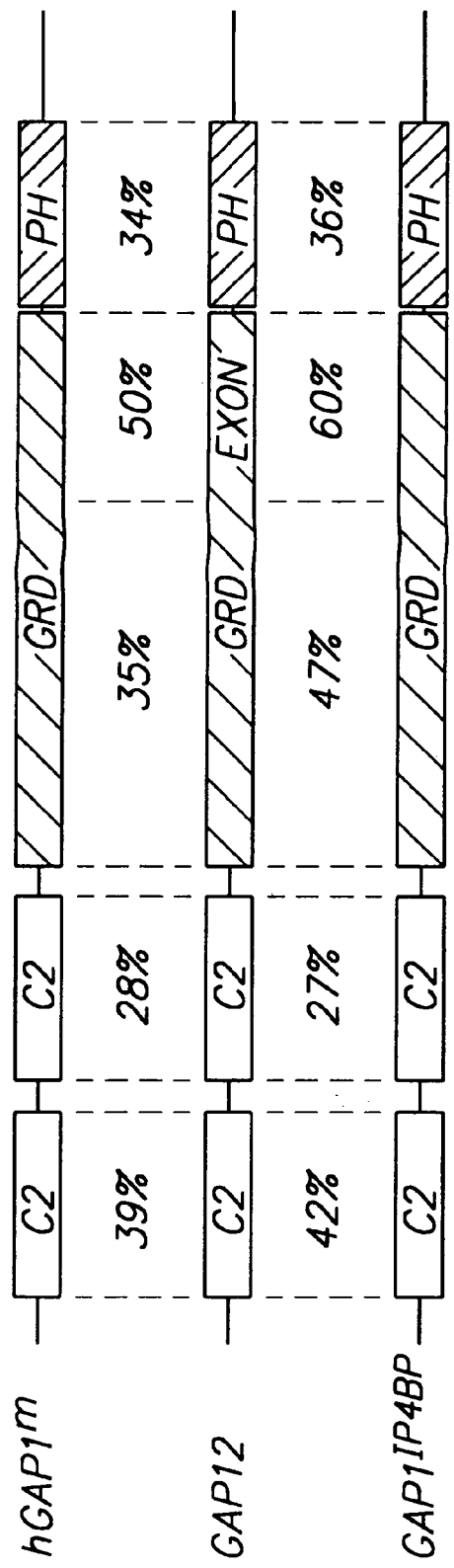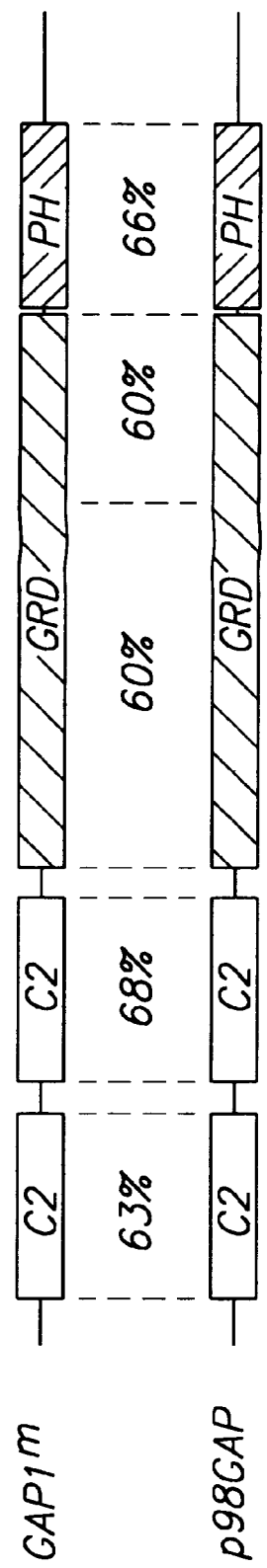
FIG. 1A
FIG. 1B

SEQUENCE LISTING

<160> NUMBER OF SEQ ID NOS: 15

<210> SEQ ID NO 1
<211> LENGTH: 3148
<212> TYPE: DNA
<213> ORGANISM: H. sapiens

<400> SEQUENCE: 1

| | | | | | |
|---|---|---|---|---|---|
| agatggaagg | ggatgttcaa | agccctccc | ttgactctga | acggacccc | agggaacatg | 60 |
| cgaccctctc | tctggcgacg | cctcccaccc | accactaata | cttgctcctg | gaccgggggg | 120 |
| cgcggaggtt | ggagagagga | ggcaggtgtc | tgcatgctac | ccgggtctcg | gacaggcggc | 180 |
| actgggacca | cgaggcaggg | agccaggctt | gaagcaggtg | acatgtagac | gtcccctggt | 240 |
| ccagcctcgg | aacctgagcg | cccttctgcc | tggaaagttt | gtggctaggc | gccatggcca | 300 |
| agagcagctc | cctgaatgtt | cgcgtggtgg | agggccgcgc | gctgcctgcc | aaggacgtgt | 360 |
| ctgggagcag | cgacccctac | tgcctagtga | aagtggacga | cgaggtggtg | gccaggacag | 420 |
| ctactgtctg | gaggagcctg | ggccccttct | gggggagga | gtacacggtg | cacctgcctc | 480 |
| tggatttcca | ccagctggcc | ttctacgtgc | tggatgagga | cactgtcggg | cacgacgaca | 540 |
| tcatcggcaa | gatctcgctg | agcagggagg | cgattacagc | cgaccccga | gggattgaca | 600 |
| gctggattaa | cttgagccga | gtggacccag | atgcagaagt | gcagggtgag | atctgcctgt | 660 |
| cagtgcagat | gctggaggat | gggcagggcc | gctgccttcg | ctgccatgtg | cttcacgcca | 720 |
| gggacctggc | tcccagagac | atctctggca | catctgaccc | atttgcacgt | gtgttttggg | 780 |
| gcagccagag | cttggagacc | tcaaccatca | agaagactcg | cttcccgcac | tgggatgaag | 840 |
| tgctggagct | gcgggagatg | ccaggtgccc | cgtccccact | gcgggtggag | ctctgggact | 900 |
| gggacatggt | gggcaagaat | gacttcttgg | gcatggtgga | gttctctcca | aagaccctcc | 960 |
| agcagaagcc | acctaaaggc | tggttccgcc | tcctgcccatt | tcccagagcc | gaggaggatt | 1020 |
| ctgggggaa | cctgggtgcc | ctgcgagtga | aggtacgcct | gattgaggac | cgcgtcctgc | 1080 |
| cctcccagtg | ctaccagcct | ctcatggagc | tgctcatgga | gtctgtgcag | gggccagcag | 1140 |
| aggaggacac | tgctagcccc | ttggctttgc | tggaagagct | gaccttgggg | gactgccgcc | 1200 |
| aggaccttgc | caccaagctg | gtgaaactct | ttcttggccg | gggactggct | gggcactttc | 1260 |
| tggactatct | cacccggcgt | gaggtggctc | ggaccatgga | ccccaacacc | ctcttccgtt | 1320 |
| ctaactccct | ggcatccaag | tcgatggaac | agtttatgaa | gctcgtgggc | atgccctacc | 1380 |
| tgcacgaggt | cctgaagcct | gtgattagcc | gtgtctttga | ggagaagaag | tacatggagc | 1440 |
| tggatccctg | caagatggac | ctgggccgca | cccggaggat | ctccttcaaa | ggcgcactct | 1500 |
| cggaggagca | gatgcgggag | accagcctgg | ggctgctgac | gggctacctg | gggcccatcg | 1560 |
| tggacgccat | cgtgggctcc | gtggggcgct | gcccgccgc | catgcgcctc | gccttcaagc | 1620 |
| agctgcaccg | gcgagtggag | gagcgcttcc | cccaggccga | gcaccaggat | gtgaagtacc | 1680 |
| tggccatcag | tggatttctc | ttcttgcgat | tcttcgcacc | tgccatcctt | accccaaagc | 1740 |

-continued

```
tgtttgacct tcgggaccaa cacgcggacc cccagactag ccgctcactg ctgttgcttg    1800
ccaaggctgt gcagagcatt ggaaacctgg gccagcagct gggccaaggc aaggaactgt    1860
ggatggcccc cctgcacccc ttcctgctgc agtgtgtctc acgtgtgaga gacttcctgg    1920
accggctggt ggatgtggat ggggatgaag ctggtgtccc agccagggcc ctgttcccgc    1980
cctcggccat tgttcgagaa ggctatctgc tgaagcgcaa ggaggagcct gccggcctgg    2040
ccacgcgctt tgccttcaag aagcgctacg tctggctcag cggggagacc ctctccttct    2100
ccaagagtcc tgagtggcag atgtgtcact ccatcccgt gtctcacatc cgcgccgtgg     2160
agcgcgtaga cgagggcgcc ttccaactgc ccacgtgat gcaggtggtg acgcaggacg     2220
gcacgggggc gctgcacacc acctacctcc agtgcaagaa tgtgaatgag ctcaaccagt    2280
ggctctcggc cttgcgcaag gccagcgccc caaccccgaa caagctggcc gcctgccacc    2340
ccggtgcctt ccgcagcgcg cgctggacct gctgcctcca ggctgagcgc tcagccgccg    2400
gctgcagccg tacacactca gctgtcaccc tgggggactg gagtgaccca ctggatcctg    2460
atgctgaggc ccagacagtg tatcggcagc tgctcctggg gcgggaccag ctcaggctga    2520
aattactgga ggattctaac atggatacaa ctctggaggc agacacaggg gcctgtcctg    2580
aggtcctggc ccgcaaaga gcagcaactg ccgcctgct ggaggtgctc gcagacctgg      2640
atcgtgccca cgaggagttc cagcagcagg agcgagggaa ggcggccctg gccccccttg    2700
gccccctaagg aaatgccaga gctagcccgg aaggaggagc aagagccagg gggccctctt   2760
cagcgcatcc tgccccggga gtctcctgtc tccttggacc tctttgattc tgtggtttgg    2820
aggctcccag agacgtgcct agtcctgtgt gccttgagtc cagaactcag ggcatggaag    2880
ccctttggca ggggccagcc ttgcactgag tgaaacttgc cctctggctt gattcagact    2940
ggagtggata ggataaggaa cctgacttat ttgactgaga ctggggtctc tacttcacca    3000
aactggcctc tatccatacc aaggaggcca gcctggcct gagctgctgg atacagctgg     3060
acctgaattc ctgatgccca tgtgatgttg ttgccccaga tgggcactaa atggcctcac    3120
tcctaaaaaa aaaaaaaaaa aaaaaaaa                                      3148
```

<210> SEQ ID NO 2
<211> LENGTH: 804
<212> TYPE: PRT
<213> ORGANISM: H. sapiens
<220> FEATURE:

<400> SEQUENCE: 2

```
Met Ala Lys Ser Ser Ser Leu Asn Val Arg Val Glu Gly Arg Ala
 1               5                  10                  15

Leu Pro Ala Lys Asp Val Ser Gly Ser Ser Asp Pro Tyr Cys Leu Val
                20                  25                  30

Lys Val Asp Asp Glu Val Val Ala Arg Thr Ala Thr Val Trp Arg Ser
                35                  40                  45

Leu Gly Pro Phe Trp Gly Glu Tyr Thr Val His Leu Pro Leu Asp
    50                  55                  60

Phe His Gln Leu Ala Phe Tyr Val Leu Asp Glu Asp Thr Val Gly His
65                  70                  75                  80

Asp Asp Ile Ile Gly Lys Ile Ser Leu Ser Arg Glu Ala Ile Thr Ala
                85                  90                  95

Asp Pro Arg Gly Ile Asp Ser Trp Ile Asn Leu Ser Arg Val Asp Pro
                100                 105                 110
```

-continued

```
Asp Ala Glu Val Gln Gly Glu Ile Cys Leu Ser Val Gln Met Leu Glu
        115                 120                 125

Asp Gly Gln Gly Arg Cys Leu Arg Cys His Val Leu His Ala Arg Asp
        130                 135                 140

Leu Ala Pro Arg Asp Ile Ser Gly Thr Ser Asp Pro Phe Ala Arg Val
145                 150                 155                 160

Phe Trp Gly Ser Gln Ser Leu Glu Thr Ser Thr Ile Lys Lys Thr Arg
                165                 170                 175

Phe Pro His Trp Asp Glu Val Leu Glu Leu Arg Glu Met Pro Gly Ala
                180                 185                 190

Pro Ser Pro Leu Arg Val Glu Leu Trp Asp Trp Asp Met Val Gly Lys
                195                 200                 205

Asn Asp Phe Leu Gly Met Val Glu Phe Ser Pro Lys Thr Leu Gln Gln
        210                 215                 220

Lys Pro Pro Lys Gly Trp Phe Arg Leu Leu Pro Phe Pro Arg Ala Glu
225                 230                 235                 240

Glu Asp Ser Gly Gly Asn Leu Gly Ala Leu Arg Val Lys Val Arg Leu
                245                 250                 255

Ile Glu Asp Arg Val Leu Pro Ser Gln Cys Tyr Gln Pro Leu Met Glu
                260                 265                 270

Leu Leu Met Glu Ser Val Gln Gly Pro Ala Glu Glu Asp Thr Ala Ser
        275                 280                 285

Pro Leu Ala Leu Leu Glu Glu Leu Thr Leu Gly Asp Cys Arg Gln Asp
        290                 295                 300

Leu Ala Thr Lys Leu Val Lys Leu Phe Leu Gly Arg Gly Leu Ala Gly
305                 310                 315                 320

His Phe Leu Asp Tyr Leu Thr Arg Arg Glu Val Ala Arg Thr Met Asp
                325                 330                 335

Pro Asn Thr Leu Phe Arg Ser Asn Ser Leu Ala Ser Lys Ser Met Glu
        340                 345                 350

Gln Phe Met Lys Leu Val Gly Met Pro Tyr Leu His Glu Val Leu Lys
        355                 360                 365

Pro Val Ile Ser Arg Val Phe Glu Glu Lys Lys Tyr Met Glu Leu Asp
        370                 375                 380

Pro Cys Lys Met Asp Leu Gly Arg Thr Arg Arg Ile Ser Phe Lys Gly
385                 390                 395                 400

Ala Leu Ser Glu Glu Gln Met Arg Glu Thr Ser Leu Gly Leu Leu Thr
                405                 410                 415

Gly Tyr Leu Gly Pro Ile Val Asp Ala Ile Val Gly Ser Val Gly Arg
                420                 425                 430

Cys Pro Pro Ala Met Arg Leu Ala Phe Lys Gln Leu His Arg Arg Val
        435                 440                 445

Glu Glu Arg Phe Pro Gln Ala Glu His Gln Asp Val Lys Tyr Leu Ala
        450                 455                 460

Ile Ser Gly Phe Leu Phe Leu Arg Phe Ala Pro Ala Ile Leu Thr
465                 470                 475                 480

Pro Lys Leu Phe Asp Leu Arg Asp Gln His Ala Asp Pro Gln Thr Ser
                485                 490                 495

Arg Ser Leu Leu Leu Leu Ala Lys Ala Val Gln Ser Ile Gly Asn Leu
                500                 505                 510

Gly Gln Gln Leu Gly Gln Gly Lys Glu Leu Trp Met Ala Pro Leu His
        515                 520                 525

Pro Phe Leu Leu Gln Cys Val Ser Arg Val Arg Asp Phe Leu Asp Arg
```

-continued

```
            530                 535                 540
Leu Val Asp Val Asp Gly Asp Glu Ala Gly Val Pro Ala Arg Ala Leu
545                 550                 555                 560

Phe Pro Pro Ser Ala Ile Val Arg Glu Gly Tyr Leu Leu Lys Arg Lys
                565                 570                 575

Glu Glu Pro Ala Gly Leu Ala Thr Arg Phe Ala Phe Lys Lys Arg Tyr
            580                 585                 590

Val Trp Leu Ser Gly Glu Thr Leu Ser Phe Ser Lys Ser Pro Glu Trp
                595                 600                 605

Gln Met Cys His Ser Ile Pro Val Ser His Ile Arg Ala Val Glu Arg
            610                 615                 620

Val Asp Glu Gly Ala Phe Gln Leu Pro His Val Met Gln Val Val Thr
625                 630                 635                 640

Gln Asp Gly Thr Gly Ala Leu His Thr Thr Tyr Leu Gln Cys Lys Asn
                645                 650                 655

Val Asn Glu Leu Asn Gln Trp Leu Ser Ala Leu Arg Lys Ala Ser Ala
            660                 665                 670

Pro Asn Pro Asn Lys Leu Ala Ala Cys His Pro Gly Ala Phe Arg Ser
            675                 680                 685

Ala Arg Trp Thr Cys Cys Leu Gln Ala Glu Arg Ser Ala Ala Gly Cys
            690                 695                 700

Ser Arg Thr His Ser Ala Val Thr Leu Gly Asp Trp Ser Asp Pro Leu
705                 710                 715                 720

Asp Pro Asp Ala Glu Ala Gln Thr Val Tyr Arg Gln Leu Leu Leu Gly
                725                 730                 735

Arg Asp Gln Leu Arg Leu Lys Leu Leu Glu Asp Ser Asn Met Asp Thr
            740                 745                 750

Thr Leu Glu Ala Asp Thr Gly Ala Cys Pro Glu Val Leu Ala Arg Gln
            755                 760                 765

Arg Ala Ala Thr Ala Arg Leu Leu Glu Val Leu Ala Asp Leu Asp Arg
            770                 775                 780

Ala His Glu Glu Phe Gln Gln Gln Glu Arg Gly Lys Ala Ala Leu Gly
785                 790                 795                 800

Pro Leu Gly Pro
```

```
<210> SEQ ID NO 3
<211> LENGTH: 3117
<212> TYPE: DNA
<213> ORGANISM: M. musculus
<220> FEATURE:
<221> NAME/KEY: CDS
<222> LOCATION: (0)...(0)

<400> SEQUENCE: 3
cgcccgggca ggtgaaccgg ctgacagcgt gcttggcccg cagctgatga catgtagggt      60
cacctcctgg tccagcctca gaacctcggc agactccttg cctggaaagt ttgggactgt     120
gcgacatggc caagagcggc tcgctgagta tccgcgtggt ggaggacga gcactgcccg      180 ccaaggacgt gtctggaagc agtgaccct attgtctggt gaaagtggat gaccaagtgg      240
tggccaggac agcaaccatc tggagggagcc tgagcccctt tgggggggag gagtacaccg    300
ttcaccttcc attggacttc caccacctgg ccttctacgt gctggatgag acaccgttg      360 gacacgatga catcattggg aagatctcat tgagcaaaga ggcgatcaca gccgacccct    420
gagggatcga cagctggatc aacctgagcc gagtggatcc agacgctgaa gtacagggtg    480
```

-continued

```
aggtctgcct ggatgtgaag ctattggagg atgctcgggg ccgctgcctc cgctgccacg      540
tgagacaggc cagggacctg gcccccaggg acatctctgg cacatcggac ccatttgccc      600
gtgtgttctg gggcaaccat agtttggaaa cttcgaccat caagaagacc cgcttcccac     660
actgggatga ggtgttggag ctgcgggagg ctccggggac cacgtccccg ctgcgagtgg      720
aactctggga ttgggacatg gtgggcaaga atgacttcct gggtatggtg gagttcaccc      780
cacagaccct gcagcagaag ccacctaatg gctggttccg gctcctgccc tttcctagag      840
ctgaggattc tggggggagc ctgggtgccc tgcggctgaa ggtgcgcctc actgaggacc      900
gggtcctgcc ttcccagtac taccagcctc tcatggaact gcttctggag tcggtgcaag      960
ggccggctga ggaggacacc accagccccc tggctctgct agaggagctg gcctctgggg     1020
actgtcgtca ggaccttgcc accaagctgg tgaagctgtt cctgggccgg ggcctggccg     1080
ggccctttct agattatctc acaaggcgtg aggtggctcg aaccaatgac cccaacaccc     1140
tcttccgttc taactccttg gcatccaagt cgatggaaca gttcatgaag ctcgtgggca     1200
tgcgctacct gcacgaggtc ctgaggccag tgatcagccg cgtcttcgag gagaagaaat     1260
atatggaact ggaccttgc aagatggacc tgaaccgctc tcggaggatc tccttcaagg     1320
gcacgcccac agaggagcag gtacgggaga ccagcctggg gctgctgacc ggatacctag     1380
ggtccgttgt ggacgccatc gtgagctcta cagggcgctg cccacttgcc ttgcgcttgg     1440
cctttaagca gctccagcgg tgtgtggaga agcgcttctc tgggatagag catcaggatg     1500
tgaagtacct ggccatcagt ggcttcctct ttctgcggtt ctttgcgcct gccatcctca     1560
caccgaaact gtttgacctc agagaccagc acgcagaccc ccagaccagc cgttccctgc     1620
tgctgctcgc caaggctgtg cagagcattg ggaacctggg ccagcagctg gccagggca      1680 aggagcagtg gctagccccg ctccatccct tcctgctgca gagcatctca cgtgtgaggg     1740
acttcctgga ccagctggtg gatgtggacg aggatgagga ggccggggt ccagcctgcg      1800 ccctggtcca accctcaacc attgttcgag aaggcttcct gctgaagcgc aaggaggagc     1860
ctggaggcct ggccacgcgc tttgccttca gaaagcgcta cttccggctg agtgggcggg     1920
acctctccta ctccaagact ccggagtggc aggttcacac atccatcccg ctgtcctgca     1980
tccgggctgt ggagcatgtg gacgagggtg cctttcaact gccacacgtc atgcaggtgg     2040
tgacacagga tggcgccggg acgtcacaca ccacctacct ccagtgtaag aacgtgaatg     2100
acttcaacca atggctgtca gccctgcgca aagccagtgc ccccaacccg ggcaagctgg     2160
ttgcctgcca ccctggtgcc ttccgcagcg ggcgctggac ctgctgcctc caggctgagc     2220
gctcagctgc tggttgtagc cgcacacact cagccatcac actgggagac tggagtgacc     2280
cactggatcc tgacgccgag gcccaggcag tgtatcgcca gctgctcctg gggcgggacc     2340
agctcaggct gaaactgctg gaggattcca gcctggacac agaagtggac cctgggaggg     2400
actccagtgc cacagacggg ccctgtgctg aggttctggc ccagcagaga gcagccacaa     2460
cccacctgct gcaggtactt gaagacttgg agcaagccca cgaggagttc cagaaacggg     2520
gataggagca agtggccctc taggatgctg gatgctgaga aagtgccaga gccagctggg     2580
gacagagcca tggggcctcc ctgagcattc tttggcccag gcatcttctt gaggccccct     2640
tcttcactgc ttggggcctc ccagacaaag cctggtcctg tgtgctctgt agccagccag     2700
ggcataggag cctttggtta gggcccagtc ttgtactgac caaacctcac tttcttctct     2760
gagcctggag tctcagcttc actggacaca gcccttccaa tacccgtggc gcccatctca     2820
ccccaagctg ctggatacag ctgtacctga acgccaaccc tggcggactc agaaaagcat     2880
```

-continued

```
tcaataggct tggccaggaa cttcctgttt tccacttctg ctagccactg tgacctcaca    2940
gatccttctg tattccactc tcatctggca gccccaacca ggtgttctca gaagaacgga    3000
ctggggcccc agcatgccaa ttcagagcct cgaagccgga cacaggctct tcctctctct    3060 tatacccctgt ataaagtgat gcgtgagcat gcttaaaaaa aaaaaaaaaa aaaaaaa      3117
```

<210> SEQ ID NO 4
<211> LENGTH: 799
<212> TYPE: PRT
<213> ORGANISM: M. musculus

<400> SEQUENCE: 4

```
Met Ala Lys Ser Gly Ser Leu Ser Ile Arg Val Glu Gly Arg Ala
 1               5                   10                  15

Leu Pro Ala Lys Asp Val Ser Gly Ser Ser Asp Pro Tyr Cys Leu Val
                20                  25                  30

Lys Val Asp Asp Gln Val Val Ala Arg Thr Ala Thr Ile Trp Arg Ser
            35                  40                  45

Leu Ser Pro Phe Trp Gly Glu Glu Tyr Thr Val His Leu Pro Leu Asp
        50                  55                  60

Phe His His Leu Ala Phe Tyr Val Leu Asp Glu Asp Thr Val Gly His
    65                  70                  75                  80

Asp Asp Ile Ile Gly Lys Ile Ser Leu Ser Lys Glu Ala Ile Thr Ala
                85                  90                  95

Asp Pro Arg Gly Ile Asp Ser Trp Ile Asn Leu Ser Arg Val Asp Pro
            100                 105                 110

Asp Ala Glu Val Gln Gly Glu Val Cys Leu Asp Val Lys Leu Leu Glu
        115                 120                 125

Asp Ala Arg Gly Arg Cys Leu Arg Cys His Val Arg Gln Ala Arg Asp
    130                 135                 140

Leu Ala Pro Arg Asp Ile Ser Gly Thr Ser Asp Pro Phe Ala Arg Val
145                 150                 155                 160

Phe Trp Gly Asn His Ser Leu Glu Thr Ser Thr Ile Lys Lys Thr Arg
                165                 170                 175

Phe Pro His Trp Asp Glu Val Leu Glu Leu Arg Glu Ala Pro Gly Thr
            180                 185                 190

Thr Ser Pro Leu Arg Val Glu Leu Trp Asp Trp Asp Met Val Gly Lys
        195                 200                 205

Asn Asp Phe Leu Gly Met Val Glu Phe Thr Pro Gln Thr Leu Gln Gln
    210                 215                 220

Lys Pro Pro Asn Gly Trp Phe Arg Leu Leu Pro Phe Pro Arg Ala Glu
225                 230                 235                 240

Asp Ser Gly Gly Ser Leu Gly Ala Leu Arg Leu Lys Val Arg Leu Thr
                245                 250                 255

Glu Asp Arg Val Leu Pro Ser Gln Tyr Tyr Gln Pro Leu Met Glu Leu
            260                 265                 270

Leu Leu Glu Ser Val Gln Gly Pro Ala Glu Glu Asp Thr Thr Ser Pro
        275                 280                 285

Leu Ala Leu Leu Glu Glu Leu Ala Ser Gly Asp Cys Arg Gln Asp Leu
    290                 295                 300

Ala Thr Lys Leu Val Lys Leu Phe Leu Gly Arg Gly Leu Ala Gly Pro
305                 310                 315                 320

Phe Leu Asp Tyr Leu Thr Arg Arg Glu Val Ala Arg Thr Asn Asp Pro
                325                 330                 335
```

-continued

```
Asn Thr Leu Phe Arg Ser Asn Ser Leu Ala Ser Lys Ser Met Glu Gln
            340                 345                 350
Phe Met Lys Leu Val Gly Met Arg Tyr Leu His Glu Val Leu Arg Pro
            355                 360                 365
Val Ile Ser Arg Val Phe Glu Glu Lys Lys Tyr Met Glu Leu Asp Pro
        370                 375                 380
Cys Lys Met Asp Leu Asn Arg Ser Arg Arg Ile Ser Phe Lys Gly Thr
385                 390                 395                 400
Pro Thr Glu Glu Gln Val Arg Gly Thr Ser Leu Gly Leu Leu Thr Gly
                405                 410                 415
Tyr Leu Gly Ser Val Val Asp Ala Ile Val Ser Ser Thr Gly Arg Cys
                420                 425                 430
Pro Leu Ala Leu Arg Leu Ala Phe Lys Gln Leu Gln Arg Cys Val Glu
            435                 440                 445
Lys Arg Phe Ser Gly Ile Glu His Gln Asp Val Lys Tyr Leu Ala Ile
        450                 455                 460
Ser Gly Phe Leu Phe Leu Arg Phe Phe Ala Pro Ala Ile Leu Thr Pro
465                 470                 475                 480
Lys Leu Phe Asp Leu Arg Asp Gln His Ala Asp Pro Gln Thr Ser Arg
                485                 490                 495
Ser Leu Leu Leu Leu Ala Lys Ala Val Gln Ser Ile Gly Asn Leu Gly
                500                 505                 510
Gln Gln Leu Gly Gln Gly Lys Glu Gln Trp Leu Ala Pro Leu His Pro
            515                 520                 525
Phe Leu Leu Gln Ser Ile Ser Arg Val Arg Asp Phe Leu Asp Gln Leu
            530                 535                 540
Val Asp Val Asp Glu Asp Glu Glu Ala Gly Gly Pro Ala Cys Ala Leu
545                 550                 555                 560
Val Gln Pro Ser Thr Ile Val Arg Glu Gly Phe Leu Leu Lys Arg Lys
                565                 570                 575
Glu Glu Pro Gly Gly Leu Ala Thr Arg Phe Ala Phe Lys Lys Arg Tyr
            580                 585                 590
Phe Arg Leu Ser Gly Arg Asp Leu Ser Tyr Ser Lys Thr Pro Glu Trp
            595                 600                 605
Gln Val His Thr Ser Ile Pro Leu Ser Cys Ile Arg Ala Val Glu His
        610                 615                 620
Val Asp Glu Gly Ala Phe Gln Leu Pro His Val Met Gln Val Val Thr
625                 630                 635                 640
Gln Asp Gly Ala Gly Thr Ser His Thr Thr Tyr Leu Gln Cys Lys Asn
                645                 650                 655
Val Asn Asp Phe Asn Gln Trp Leu Ser Ala Leu Arg Lys Ala Ser Ala
            660                 665                 670
Pro Asn Pro Gly Lys Leu Val Ala Cys His Pro Gly Ala Phe Arg Ser
        675                 680                 685
Gly Arg Trp Thr Cys Cys Leu Gln Ala Glu Arg Ser Ala Ala Gly Cys
        690                 695                 700
Ser Arg Thr His Ser Ala Ile Thr Leu Gly Asp Trp Ser Asp Pro Leu
705                 710                 715                 720
Asp Pro Asp Ala Glu Ala Gln Ala Val Tyr Arg Gln Leu Leu Leu Gly
                725                 730                 735
Arg Asp Gln Leu Arg Leu Lys Leu Leu Glu Asp Ser Ser Leu Asp Thr
            740                 745                 750
```

```
Glu Val Asp Pro Gly Arg Asp Ser Ser Ala Thr Asp Gly Pro Cys Ala
            755                 760                 765

Glu Val Leu Ala Gln Gln Arg Ala Ala Thr Thr His Leu Leu Gln Val
            770                 775                 780

Leu Glu Asp Leu Glu Gln Ala His Glu Glu Phe Gln Lys Arg Gly
785                 790                 795

<210> SEQ ID NO 5
<211> LENGTH: 20
<212> TYPE: DNA
<213> ORGANISM: H. sapiens

<400> SEQUENCE: 5
cctgtgtgca tccacatctg                                              20

<210> SEQ ID NO 6
<211> LENGTH: 20
<212> TYPE: DNA
<213> ORGANISM: H. sapiens

<400> SEQUENCE: 6
ctccaagagt cctgagtggc                                              20

<210> SEQ ID NO 7
<211> LENGTH: 27
<212> TYPE: DNA
<213> ORGANISM: H. sapiens

<400> SEQUENCE: 7
gcggaattca tcatgcgtga ttacaag                                      27

<210> SEQ ID NO 8
<211> LENGTH: 27
<212> TYPE: DNA
<213> ORGANISM: H. sapiens

<400> SEQUENCE: 8
gaggaattcc tagagcagca gacatga                                      27

<210> SEQ ID NO 9
<211> LENGTH: 27
<212> TYPE: DNA
<213> ORGANISM: H. sapiens

<400> SEQUENCE: 9
gaggaattca tgcgcgagta caaagtg                                      27

<210> SEQ ID NO 10
<211> LENGTH: 27
<212> TYPE: DNA
<213> ORGANISM: H. sapiens

<400> SEQUENCE: 10
gcggaattcc tattgtatgt tacatgc                                      27

<210> SEQ ID NO 11
<211> LENGTH: 18
<212> TYPE: PRT
<213> ORGANISM: H. sapiens

<400> SEQUENCE: 11

Val Glu Phe Ser Pro Lys Thr Leu Gln Gln Lys Pro Pro Lys Gly Trp
 1               5                  10                  15
```

Phe Arg

```
<210> SEQ ID NO 12
<211> LENGTH: 18
<212> TYPE: PRT
<213> ORGANISM: H. sapiens

<400> SEQUENCE: 12

Thr Leu Gly Asp Trp Ser Asp Pro Leu Asp Pro Asp Ala Glu Ala Gln
 1               5                  10                  15
Thr Val

<210> SEQ ID NO 13
<211> LENGTH: 20
<212> TYPE: DNA
<213> ORGANISM: H. sapiens

<400> SEQUENCE: 13
cctgtgtgca tccacatctg                                                    20

<210> SEQ ID NO 14
<211> LENGTH: 20
<212> TYPE: DNA
<213> ORGANISM: H. sapiens

<400> SEQUENCE: 14
ctccaagagt cctgagtggc                                                    20

<210> SEQ ID NO 15
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(12)
<223> OTHER INFORMATION: Xaa = Any Amino Acid

<400> SEQUENCE: 15

Phe Leu Arg Xaa Xaa Xaa Pro Ala Xaa Xaa Xaa Pro
 1               5                  10
```

GAP12 GENES AND THEIR USES

BACKGROUND

Eukaryotic cells contain a number of small GTPases that act as intermediates in signal transduction. The Ras family of GTPases includes Ras and Ras-like proteins, which control of cell growth and differentiation, the Rho and Rac proteins that regulate cytoskeletal organization, and the Rab and Ran proteins that regulate vesicular sorting. Ras proteins play an important role in the regulation of cellular proliferation through intracellular signaling pathways in which binding of an extracellular signal molecule to a tyrosine kinase receptor is transmitted to the cell nucleus, resulting in the initiation of transcription of specific genes.

Similar to other guanine-binding proteins (such as the heterotrimeric G proteins), the Ras proteins cycle between an active guanosine-triphosphate (GTP) bound form and an inactive, guanosine-diphosphate (GDP) bound form. The balance of these two states determines the decision to undergo division. The weak intrinsic GTPase activity of Ras proteins is greatly enhanced by the action of GTPase activating proteins (GAPs). Point mutations have been described in Ras genes ('activating' or oncogenic mutants) that decrease the intrinsic GTPase activity of Ras and render it insensitive to stimulation by GAPs. GAP genes are also known for the other families of small GTPases.

Tumor susceptibility genes may be oncogenes, which are typically upregulated in tumor cells, or tumor suppressor genes, which are down-regulated or absent in tumor cells. Malignancies may arise when a tumor suppressor is lost and/or an oncogene is inappropriately activated. When such mutations occur in somatic cells, they result in the growth of sporadic tumors. Familial predisposition to cancer may occur when there is a mutation, such as loss of an allele encoding a tumor suppressor gene, present in the germline DNA of an individual.

Abnormal signal transduction involving activated Ras genes plays a major role in the development of a variety of tumors. Ras genes are mutated in approximately 30% of all human tumors, suggesting a key role in a number of different cell types. GAP proteins may also have a role in abnormal growth control, because they increase GTPase activity in the bound protein, thereby shifting the balance in the cell to the inactive, GDP binding form. GAP activity has been demonstrated to result from a catalytic domain termed the GAP Related Domain (GRD). Neurofibromin, the product of the NF1 gene contains a GRD and possesses GAP activity towards ras subfamily members. It has been shown that a predisposition to neurofibromatosis is correlated with mutations in the NF-1 gene.

More recently a family of RasGAPs have been identified that share multiple conserved motifs: two C2 domains, homologous to the C2 regulatory region of protein kinase C, a GRD and a pleckstrin homology domain. This arrangement was first observed in the Drosophila GAP1 gene and has since been identified in four mammalian GAPs, rat GAP1$^m$, human GAP1$^{IP4BP}$, bovine P98GAP, and mouse GAPIII. These proteins can be collectively grouped as the rasGAP1 family. Outside of the GRD, the p120GAP, NF1 and GAP1 proteins are dissimilar and possess additional motifs that may serve to regulate GAP catalytic activity or the interaction of these proteins with other cellular signaling molecules.

The involvement of GAP proteins with regulation of Ras and Ras-like protein activity, and the association with tumor development makes the further identification of novel GAP genes of great interest.

RELEVANT LITERATURE

Decreased expression of Ras GTPase activating protein in human trophoblastic tumors is described in Stahle-Backdhal et al. (1995) *Am. J. Pathol.* 146:1073–1078. The role of Ras GTPase activating protein in human tumorigenesis is reviewed in Friedman (1995) *Pathobiology* 63:348–350. The molecular genetics of neurofibromatosis type I is reviewed in Shen et al. (1996) J. Med. Genet. 33:2–17; the disease is reviewed in OMIM 162200.

The sequence of related genes may be accessed at Genbank as follows: NF1, no. M89914; p120 GAP, no. P20936; IQGAP1, no. L33075; IQGAP2, no. U51903. Amino acids that are present in catalytically active GAP proteins are identified in Scheffzek et al. (1996) *Nature* 384:591–596; and Ahmadian et al. (1996) *J Biol Chem* 271:16409–16415.

SUMMARY OF THE INVENTION

Isolated nucleotide compositions and sequences are provided for GAP12 (GAP12) genes. The GAP12 nucleic acid compositions find use in identifying homologous or related genes; in producing compositions that modulate the expression or function of its encoded protein, GAP12; for gene therapy; mapping functional regions of the protein; and in studying associated physiological pathways. In addition, modulation of the gene activity in vivo is used for prophylactic and therapeutic purposes, such as treatment of cancer, identification of cell type based on expression, and the like.

BRIEF DESCRIPTION OF THE DRAWINGS

FIGS. 1A and 1B show a domain sequence comparison between GAP12 and other GAP1 family members. FIG. 1A is a schematic of the GAP1 conserved domains, indicating the percent peptide identity between GAP12 and the human version of GAP1m, and GAP12 and human GAP1$^{IP4BP}$. FIG. 1B is a schematic demonstrating the higher level of conservation of rat GAP1m to p98GAP than either protein to GAP12.

DESCRIPTION OF THE SPECIFIC EMBODIMENTS

Nucleic acid compositions encoding GAP12 (GAP12) are provided. They are used in identifying homologous or related genes; in producing compositions that modulate the expression or function of its encoded protein; for gene therapy; mapping functional regions of the protein; and in studying associated physiological pathways. The GAP12 gene product is a member of the GTPase activating protein family. It has a high degree of homology to known RasGAP proteins, which increase the GTPase activity of Ras or Ras-related proteins.

Modulation of GAP12 gene activity in vivo is used for prophylactic and therapeutic purposes, such as treatment of cancer, investigation of Ras signaling pathway function, identification of cell type based on expression, and the like. The protein is useful as an immunogen for producing specific antibodies, in screening for biologically active agents that act in the Ras signaling pathway and for therapeutic and prophylactic purposes.

Characterization of GAP12

The sequence data predict that GAP12 is a GTPase activating protein. The human gene sequence is provided as SEQ ID NO:1, the encoded polypeptide product as SEQ ID NO:2, the mouse homolog as SEQ ID NO:3, and its encoded product as SEQ ID NO:4. The mouse and human genes encode 804 and 799 amino acid polypeptides respectively. The gene product sequence is consistent with an ability to activate specific small GTPases, which include the superfamily of proteins that have sequence similarity to p21 Ras. The chromosomal location of the human gene has been localized to 12q23–24. It is predicted that the human GAP12 gene product is a tumor suppressor gene.

Sequence analysis of these two proteins revealed the presence of two N-terminal calcium dependent phospholipid binding C2 domains, a conserved GAP related domain (GRD) and a C-terminal PH domain, as previously observed in the rat GAP1$^m$, human Gap1$^{IP4BP}$, mouse GAPIII, bovine p98GAP and D. melanogaster GAP1 proteins.

Many components of the Ras signaling pathway have been identified and characterized, including members of the Ras, Ran, Rab and Rho families, Raf kinases, p190 binding protein, etc. The availability of isolated genes and gene products in this pathway allows the in vitro reconstruction of the pathway and its regulation, using native or genetically altered molecules, or a combination thereof.

GAP12 is highly expressed in endocrine tissue, particularly the follicular cells of the thyroid and the adrenal medulla, and at lower levels in adult brain, spinal cord, prostate, ovary and testis. This pattern of expression may reflect the involvement of the GAP12 protein in regulating functions specific to these cell types, such as the secretion of hormones. The expression data suggest that the role of rasGAP proteins is not limited to downregulation of cellular proliferation and differentiation. In particular, the regulation by GTPases of signaling pathways leading to secretion of biologically active peptides and other biomolecules may be regulated by GAP proteins. GAP12 may play a role in the regulation of the secretory response.

Identification of GAP12 Sequences

Homologs of GAP12 are identified by any of a number of methods. A fragment of the provided cDNA may be used as a hybridization probe against a cDNA library from the target organism of interest, where low stringency conditions are used. The probe may be a large fragment, or one or more short degenerate primers.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). Nucleic acids that are substantially identical to the provided GAP12 sequences, e.g. allelic variants, genetically altered versions of the gene, etc., bind to the provided GAP12 sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between mammalian species, e.g. human and mouse, homologs have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) J Mol Biol 215:403–10. The sequences provided herein are essential for recognizing GAP12 related and homologous proteins in database searches.

GAP12 Nucleic Acid Compostions

Nucleic acids encoding GAP12 may be cDNA or genomic DNA or a fragment thereof. The term "GAP12 gene" shall be intended to mean the open reading frame encoding specific GAP12 polypeptides, introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a GAP12 protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where GAP12 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) Mol Med 1: 194–205; Mortlock et al. (1996) Genome Res. 6: 327–33; and Joulin and Richard-Foy (1995) Eur J Biochem 232: 620–626.

The regulatory sequences may be used to identify cis acting sequences required for transcriptional or translational regulation of GAP12 expression, especially in different tissues or stages of development, and to identify cis acting sequences and trans acting factors that regulate or mediate GAP12 expression. Such transcription or translational control regions may be operably linked to a GAP12 gene in order to promote expression of wild type or altered GAP12 or other proteins of interest in cultured cells, or in embryonic, fetal or adult tissues, and for gene therapy.

The nucleic acid compositions of the subject invention may encode all or a part of the subject polypeptides. Double or single stranded contiguous fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Such small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The GAP12 genes are isolated and obtained in substantial purity, generally as other than an intact chromosome. Usually, the DNA will be obtained substantially free of other nucleic acid sequences that do not include a GAP12 sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of GAP12 gene expression in the sample.

The sequence of a GAP12 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al, *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989). Such mutated genes may be used to study structure-function relationships of GAP12, or to alter properties of the protein that affect its function or regulation.

GAP12 Polypeptides

The subject gene may be employed for producing all or portions of GAP12 polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a GAP12 gene, or may be derived from exogenous sources.

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the GAP12 gene in eukaryotic cells, where the GAP12 protein will benefit from native folding and post-translational modifications. Small peptides can also be synthesized in the laboratory. Peptides that are subsets of the complete GAP12 sequence may be used to identify and investigate parts of the protein important for function, such as the GTPase binding domain, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed GAP 12 polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of GAP12. Antibodies may be raised to isolated peptides corresponding to these domains, or to the native protein. For example, antisera that detect GAP12 polypeptides in Western blots have been raised against the polypeptides [SEQ ID NO:11] VEFSPKTLQQKPPKGWFR; and [SEQ ID NO:12] TLGD-WSDPLDPDAEAQTV.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Diagnostic Uses

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in a GAP12 coding region or control regions is associated with disease, particularly cancers, e.g. germ cell cancers, choriocarcinomas, endocrine tissue abnormalities, etc. Disease associated polymorphisms may include deletion or truncation of the gene, mutations that alter expression level, that affect the binding activity of the protein to the cognate GTPase, etc.

Changes in the promoter or enhancer sequence that may affect expression levels of GAP12 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express GAP12 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms,for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl 6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type GAP12 sequence. Hybridizationwith the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in GAP12 may be based on the functional or antigenic characteristics of the protein. Protein truncation assays are useful in detecting deletions that may affect the biological activity of the protein. Various immunoassays designed to detect polymorphisms in GAP12 proteins may be used in screening. Where many diverse genetic mutations lead to a particular disease phenotype, functional protein assays have proven to be effective screening tools. The activity of the encoded GAP12 protein in GTPase activation, binding or Ras-related proteins, etc., may be determined by comparison with the wild-type protein.

Antibodies specific for a GAP12 may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal GAP12 in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Diagnostic screening may also be performed for polymorphisms that are genetically linked to a disease predisposition, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) Genomics 24:225–233; Ziegle et al. (1992) Genomics 14:1026–1031; Dib et al., supra.

Modulation of Gene Expression

The GAP12 genes, gene fragments, or the encoded protein or protein fragments are useful in gene therapy to treat disorders associated with GAP12 defects. Expression vectors may be used to introduce the GAP12 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or GAP12 protein may be introduced into tissues or host cells by any number of routes, including viral infection, microinjection, or fusion of vesicles. Jet injection may also be used for intramuscular administration, as described by Furth et al. (1992) Anal Biochem 205:365–368. The DNA may be coated onto gold microparticles, and delivered intradermally by a particle bombardment device, or "gene gun" as described in the literature (see, for example, Tang et al. (1992) Nature 356:152–154), where gold micro projectiles are coated with the GAP12 or DNA, then bombarded into skin cells.

Antisense molecules can be used to down-regulate expression of GAP12 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnology 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate,3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

Genetically Altered Cell or Animal Models for GAP12 Function

The subject nucleic acids can be used to generate transgenic animals or site specific gene modifications in cell lines. Transgenic animals may be made through homologous recombination, where the normal GAP12 locus is altered. Alternatively, a nucleic acid construct is randomly integrated into the genome. Vectors for stable integration include plasmids, retroviruses and other animal viruses, YACs, and the like.

The modified cells or animals are useful in the study of GAP12 function and regulation. For example, a series of small deletions and/or substitutions may be made in the GAP12 gene to determine the role of different exons in oncogenesis, signal transduction, etc. Of interest are the use of GAP12 to construct transgenic animal models for cancer, where expression of GAP12 is specifically reduced or absent, e.g. in endocrine tissue, etc. Specific constructs of interest include anti-sense GAP12, which will block GAP12 expression, expression of dominant negative GAP12 mutations, and over-expression of Ras genes. A detectable marker, such as lac Z may be introduced into the GAP12 locus, where upregulation of GAP12 expression will result in an easily detected change in phenotype.

One may also provide for expression of the GAP12 gene or variants thereof in cells or tissues where it is not normally expressed or at abnormal times of development. By providing expression of GAP12 protein in cells in which it is not normally produced, one can induce changes in cell behavior, e.g. through GAP12 mediated Ras activity modulation.

DNA constructs for homologous recombination will comprise at least a portion of the GAP12 gene with the desired genetic modification, and will include regions of homology to the target locus. For example, the mouse 43A4 exon or exon 1 may be used as a source of homologous sequences for a knock-out construct. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females.

The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on Ras or related gene activation, oncogenesis, etc.

In Vitro Models for GAP12 Function

The availability of a number of components in the Ras signaling pathway, as previously described, allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other; utilization of GTP, etc. The components may be modified by sequence deletion, substitution, etc. to determine the functional role of specific domains.

Drug screening may be performed using an in vitro model, a genetically altered cell or animal, or purified GAP12 protein. One can identify ligands or substrates that bind to, modulate or mimic the action of GAP12. Areas of investigation include the development of cancer treatments, metastasis, etc. The relationship between Ras and related proteins, and GAP proteins suggests that agents that modulate each of these protein activities will have antagonistic activities.

Drug screening identifies agents that provide a replacement for GAP12 function in abnormal cells. Agents that mimic its function, in terms of Ras or related gene down-regulation are predicted to inhibit the process of oncogenesis. Conversely, agents that reverse GAP12 function may stimulate controlled growth and healing. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, such as GTPase binding, etc.

The term "agent" as used herein describes any molecule, e.g. protein or pharmaceutical, with the capability of altering or mimicking the physiological function of GAP12. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic GAP12 function, such as repression of Ras activity, binding properties, etc. For example, an expression construct comprising a GAP12 gene may be introduced into a cell line under conditions that allow expression. The level of GAP12 activity is determined by a functional assay, as previously described. In one screening assay, candidate agents are added in combination with GTPase protein, and the ability to down-regulate its activity is detected. In another assay, the ability of candidate agents to enhance GAP12 function is determined. Alternatively, candidate agents are added to a cell that lacks functional GAP12, and screened for the ability to reproduce GAP12 in a functional assay.

The compounds having the desired pharmacological activity may be administered in a physiologically acceptable carrier to a host for treatment of cancer, etc. The compounds may also be used to enhance GAP12 function in wound healing, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Methods and Materials

Exon isolation and cDNA screening. The cosmid library LANL12 is described in Troffater et al. (1995) *Genome Res.* 5: 214–224. The library was submitted to large scale exon amplification as described in Church et al. (1994) *Nature Genet.* 6:98–105. Recovered exons were sequenced and analyzed using blast homology searches (Pearson and Lipman (1988) *Proc. Natl . Acad. Sci. USA*. 85:2444–2448). Exon 43A4 (SEQ ID NO:1, position 1674–1950) was PCR amplified from the vector using vector primers as described previously in Church et al. (1994) *Hum Mol. Genet.* 2:1915–1920. The resulting product was gel purified and radiolabeled with [$^{32}$P] dCTP (Amersham) using the random primer method of Feinberg and Vogelstein (1984) *Hum Mol. Genet.* 2:1915–1920. This product was used to probe approximately 1.4×10$^6$ recombinant phage plaques of a adult frontal cortex cDNA library in λzapII (B616, Stratagene) under standard high stringency conditions.

To isolate cDNA for the mouse homolog of GAP12, human exon 43A4 probe was used to screen 1.3×10$^6$ plaques of a mouse teratocarcinoma cDNA library (PCC4, Stratagene) using low stringency hybridization conditions (40% dimethylformamide, 10% dextran sulphate, 42° C., 48 hours).

Recovered cDNA clones were sequenced using standard ABI dye-primer and dye-terminator chemistry on a 377 automated DNA sequencer. The 5' terminal sequences were isolated by 5' extension using a nested primer strategy on adult brain cDNA from human or mouse RNA provided with the marathon ready rapid amplification of cDNA ends (RACE) PCR kit from Clontech.

Chromosomal localization of the GAP12 locus. End sequences were obtained from the chromosome 12 cosmid 89G8 after Sac I digestion and religation to reduce the insert size. Primers, G8A [SEQ ID NO:5] (5'CCTGTGTGCATCCACATCTG3') and G8B [SEQ ID NO:6] (5'CTCCMGAGTCCTGAGTGGC 3') were designed to amplify a 290 bp product across the GENEBRIDGE 4 radiation hybrid panel (http://-genome.wi.mit.edu/cgi-bin/contig/rhmapper.pl). PCR data were submitted to this URL for automatic 2 point linkage analysis.

Expression analysis by northern and In situ hybridization. Human adult and fetal multiple tissue northern blots (Clontech) were prehybridised at 42° C. in 50% formamide, 10% dextran sulphate, 0.8M NaCl, 5× Denhardt's solution, 0.1% sodium pyrophosphate, 50 mM Tris pH 7.5), 100 μg/ml sheared denatured salmon sperm DNA, 0.5% SDS. Exon 43A4 was radiolabeled as described above and hybridisations were performed overnight. Filters were washed to under final stringency conditions of 1×SSC, 0.1% SDS at 65° C. and exposed to autoradiographic film.

Tissue mRNA in situ hybridization was performed on sections of mouse tissues and embryos, using $^{35}S$ -labeled sense and antisense riboprobes made by the in vitro transcription, using T3 and T7 polymerases, of a 313 bp Alu I pBluescript KS (Stratagene) subclone. This clone contained the last 183 nt of the mGAP12 ORF and 130 bp of 3'UTR (mouseGAP12 nucleotides 2342–2655). Hybridization was in 50% formamide, 10% dextran sulphate, 1× Denhardts, for 16 hrs at 55° C. Following hybridization the slides were washed once in 5×SSC, 0.1% BME at 55° C. for 30 minutes, three times in 50% formamide, 2×SSC, 0.1% BME, at 65° C. for 30 minutes and three times 15 minutes in wash buffer (0.5 M NaCl, 10 mM Tris-HCl, 5 mM EDTA) at 37° C. The slides were then treated with 20 μg/ml RNAse in wash buffer for 30', washed three times 15 minutes with wash buffer, one times 15 minutes in 2×SSC, 37° C. and one times 15 minutes in 0.1×SSC at 37° C. Following air drying the slides were dipped in NTB-2 nuclear emulsion (Kodak) and exposed for 14–18 days at 4° C. with dessication. The slides were developed and counterstained with toludine blue (Sigma).

Expression of GAPs and GTPases in E. coli-Catalytic GAP related domain of human GAP12. An Eco RI insert from a cDNA clone containing amino acid residues 240 to the C-terminus, was inserted into the Eco RI site of pGEX2T (Pharmacia) and expressed in DH5α cells as a fusion protein with glutathione S transferase. A second pGEX2T construct was produced by fusing a cDNA clone with sequences from the 5'RACE PCR product, encoding amino acids 106 to the C-terminus. Inductions were at 0.1 mM IPTG for three hours at 30° C. Cells were lysed by sonication in buffer A (50 mM NaCl, 50 mM Tris HCl PH 7.5, 5 mM $MgCl_2$) supplemented with 1 mM DTT, 1 mM PMSF and 10 mg/ml of pefabloc (Boehringer Mannheim). After removal of cellular debris the soluble fraction was incubated with a 50% slurry of glutathione agarose beads (Sigma) at 4° C. for 30 minutes. Beads were collected by centrifugation, washed in buffer A and eluted as a fusion protein with a glutathione elution buffer (100 mM Tris HCl pH 8.0, 120 mM NaCl) for 30 minutes at 4° C. Protein was concentrated using p30 centricon columns (Amicon), snap frozen and stored as aliquots in liquid nitrogen.

Positive control GAP protein. A full length fusion protein expressing rat GAP1$^m$ (Maekawa et al. (1994) *Mol. Cell. Biol.* 14:6879–6885) in pGEX2T was used as a positive control. Protein was prepared as for the GAP12 constructs, after a 16 hour induction at 0.1 mM IPTG at 25° C.

GTPase substrates for the GAP assay. PGEX 2T constructs expressing full length H-Ras, R-Ras, Ral A and TC21 were used. Constructs expressing rap1a and rap2a were created by amplifying these genes from two IMAGE cDNA clones, (#45166 and 321529), which had 100% sequence identity to the rap1a and rap2a sequences respectively. Oligos containing an EcoRI linker were designed as follows; rap1a-1 [SEQ ID NO:7] (5'GCGGAATTCATCATGCGTGATTACAAG 3') and rap1a-2 [SEQ ID NO:8] (5'GAGGAATTCCTAGAGCAGCAGACATGA 3'), rap2a-1 [SEQ ID NO:9] (5'GAGGMTTCATGCGCGAGTACAAAGTG 3') and rap2a-2 [SEQ ID NO:10] (5'GCGGAATTCCTATTGTATGTTACATGC3'). These PCR products were cleaved with Eco RI and ligated into the Eco RI site of pGEX2T. Inductions and protein preparation were as for GAP12.

Assay for GAP activity. GTPase substrates were diluted to 0.008 mg/ml in buffer A and 4 μl was loaded with 1 μl [γ-$^{32}$P GTP] (Amersham, 5000 Ci/mmol) in 25 mM NaCl, 20 mM Tris-HCl pH 7.0, 0.1 mM DTT, and 5 mM EDTA at 30° C. for 10 minutes before the addition of $MgCl_2$ to 20 mM. Purified GAP12 and GAP1$^m$ fusion proteins (~150 ng) were mixed with 3 μl of loaded GTPase in a 30 μl reaction at 30° C. 8 μl aliquots were removed from the reaction at 1, 5 and 10 minute intervals and quenched in 1 ml of ice cold buffer A to halt the reaction. These samples were filtered through nitrocellulose membranes (Schleicher and Schuell), washed with 2×5 ml of cold buffer A and the level of filter bound radioactivity was analyzed by liquid scintillation counting.

Results

Full length cloning of human GAP12 and mRNA expression analysis. A 285 bp exon containing the PROSITE consensus motif for a GTPase activating protein; SEQ ID NO:15 FLR(XXX)PA(XXX)P was identified during large scale exon amplification from a chromosome 12 cosmid library. Six overlapping cDNA clones were isolated from the human frontal cortex library after screening with the exon sequence. The largest clone contained 2535 bp of unique sequence. A further 578 bp of 5' sequence was obtained from 5' extension products recovered during RACE PCR from an adult brain mRNA source. The largest open reading frame predicted a protein of 804 amino acids. A TGA termination codon was present 39 bp upstream of the start methionine residue and a loose Kozak consensus sequence was observed [GCACCATGG]. The 420 bp 3'UTR was confirmed by 3'RACE analysis.

Northern blot analysis using one cDNA clone indicated the presence of a 3.0–3.3 kb RNA species in a number of human tissues, corresponding to the full length open reading frame. Relative expression levels were high in the adult adrenal and thyroid, moderate in trachea and brain and low in the spinal cord, stomach, prostate, ovary and testis. Of four tissues analyzed on a human fetal northern blot, expression was demonstrated to be very high in the kidney and low in the brain.

Full length cloning of mouse GAP12 and murine mRNA analysis. The mouse homolog of GAP12 (herein "musgap12") was isolated for comparative sequence analysis and to enable more detailed analysis of the endocrine tissue expression patterns by mRNA in situ hybridization studies. Four overlapping cDNA clones were identified during low stringency screening of a mouse teratocarcinoma cDNA library with the human exon probe, and 233 bp of 5' sequence was obtained by 5' RACE using a mouse brain mRNA source. The longest predicted open reading frame encoded an 799 amino acid protein with 92% similarity (87% identity) to the human gene.

In situ hybridization experiments using a 313 bp mus-GAP12 riboprobe confirmed the presence of GAP12 mRNA when hybridized with sections of mouse adrenal and thyroid tissues. Hybridization of GAP12 mRNA to thyroid tissue sections showed that it was specifically expressed in the follicular cells that are responsible for thyroid hormone production and secretion. GAP12 mRNA expression in the adrenal gland appears to be mainly in the medullary cells, with some specific staining in the cells of the outer cortex.

Structural analysis of GAP12 protein. Analysis of amino acid similarities was performed using blast searches against the Swissprot. A summary of the domains identified and their similarity to other members of the mammalian GAP1 family is presented in FIG. 1. The exon trapped product encoded amino acids from the most highly conserved carboxyl region of the GRD, residues 458 to 553, and is 61% identical (80% similar) to the GAP1 proteins, drosophila GAP1, bovine p98GAP, human GAP1$^{IP4BP}$ and mouse GAPIII, 55% identical (79% similar) to rat GAP1m, 50% identical (77% similar) to human GAP1$^m$ and a 45% identical (74% similar) to p120rasGAP. The conservation of amino acid identity across the amino-terminus of the GRD falls to between 37–41% (FIG. 1a). This is a lower level of amino acid identity than is observed between the other GAP1 family members. Bovine p98GAP and mouse GAPIII share 93–96% amino acid identity across their full length sequence and an 87% identity with human GAP1$^{IP4BP}$. Rat GAP1$^m$ is more diverged, sharing only 61–68% identity with the three other mammalian GAP1 family members, represented by p98GAP in FIG. 1b. Although the overall identity with other GAP1 family members is low, the GAP12 peptide encodes all four of the domains found in the other proteins. The first C2 domain is approximately 40% identical to those found in the other family members, however the second C2 domain is more diverged and shows greatest sequence identity (~65%) to the original C2 domain found in mammalian PKC (genbank accession number M13977). The pleckstrin homology (PH) domain is most closely related to that found in the GAP1$^m$ protein.

Alignments with the GRD's of five rasGAP proteins catalytically active against p21$^{ras}$ and the two rasGAP-related proteins IQGAP1 and IQGAP2 indicate that GAP12 possesses a relatively well conserved full length GRD. All of the 25 amino acids previously identified as invariant or highly conserved in rasGAP are present in GAP12 with the exception of the leucine, which is a lysine in GAP12. This residue is towards the amino terminus of the minimal catalytic domain required for p120GAP and upstream of the minimum domain defined for NF1, so a divergence at this position may not be important in defining the catalytic activity of GAP12. Mutations in the invariant residues R, FLR (positions 233–235), K (position 280) and N (position 288) in p120GAP or NF1, have been described as interfering with GAP activity. However, each of these residues is present in GAP12. In contrast to these similarities, alignment of the catalytically active rasGAP proteins to the GAP12, Sar1 and IQGAP peptides is interrupted (positions 138–152) by an additional 17 residues found in GAP12 (and musGAP12). The Sar1 and IQGAP1 and IQGAP2 peptides encode an additional 20–23 residues in the same region. These three proteins have other breaks in their alignments with the basic GRD due to the presence of 4–6 additional residues in three other regions.

GAP activity assay of GAP12. The amino acid similarities of the GAP12 GRD indicated that this protein was most likely to function as a GAP towards members of the ras subfamily of small GTPases. To further investigate this hypothesis, GAP activity assays were performed to test the effect of the GAP12 protein on the rate of GTP hydrolysis of small GTPases. Full length GAP12 in the bacterial expression vector pGEX was insoluble, therefore two N-terminally truncated fusion constructs of GAP12 were created encoding aminos acids 106-C-terminus and 204-C-terminus. Soluble recombinant proteins from these clones were recovered and tested for GAP activity. A full length GST-ratGAP1$^m$ fusion protein was prepared in parallel as a control for enzyme preparation and to validate the GAP assay reagents. This was shown to stimulate the GTPase activity of H-ras, R-ras, and TC21 in these experiments. However, the two proteins encompassing the GAP12 GRD did not show any evidence for elevating or inhibiting the intrinsic GTPase activity of these small GTPase molecules or of rap1b, rap2a or ral A.

Chromosomal localization of human GAP12. Radiation hybrid mapping performed on sequences from the GAP12 human cDNA was not successful due to the high sequence conservation between the human and hamster genes, resulting in amplicons from both species. However, exon 43A4 was mapped back to one of the cosmids used for the exon amplification experiment. Primers were designed to amplify a 290bp product from a single copy 89G8 end sequence. This was amplified from across the GENEBRIDGE 4 radiation hybrid panel and automatic two point linkage analysis at (http://-genome.wi.mit.edu/cgi-bin/contig/rhmapper.pl) indicated that this cosmid mapped approximately 3.98 CR (680 Kb) away from the framework marker WI1432 corresponding to cytoband 12q23–24.

Discussion

Full length sequences for a novel human protein and a mouse homolog have been isolated. The gene identified in this study is a novel member of the rasGAP family, based upon the presence of amino acids which are conserved in the GRD of all known rasGAP proteins. In particular, all of the residues demonstrated to be essential for GAP activity toward ras family members are present in GAP12. Structurally the GAP12 protein appears to be most closely related to members of the GAP1 family, each of which encodes four conserved domains: two N-terminal C2 domains, a central GRD and a C-terminal PH domain.

The C2 domains in the GAP1 family show similarity to the C2 regulatory domain of protein kinase C and are present in all of the rasGAP family members except for the yeast IRA and Sar1 proteins. This domain is found in a number of proteins, synaptotagmin, rhabphilin 3A and phospholipase C, that interact with membrane phospholipids in a Ca$^{2+}$ dependent manner. Their precise function in the GAP1 family is not known, but it has been proposed that these domains may serve to regulate the translocation and activity of the GAP proteins upon Ca$^{2+}$ influx or in the presence of certain phospholipids. Consistent with this theory is the observation that the GAP activity of p120GAP is inhibited in the presence of certain mitogenic lipids such as arachidonic acid and phosphatidic acid. The pleckstrin homology (PH) domain is a commonly occurring signaling molecule. As a small domain, around 100 amino acids, which is often found adjacent to other functional domains it is thought unlikely that the PH domain functions independently, but instead regulates other functional domains. Recently it has been shown that the PH domain of GAP1$^m$ binds inositol 1,3,4,5-tetrakisphosphate (IP$_4$). The human GAP1 protein, GAP1$^{IP4BP}$ was previously shown to bind this molecule, though the binding domain was not identified. This domain of GAP1$^m$ also bound phospholipids in a Ca$^{2+}$ independent manner. The PH domain may serve to facilitate GAP interaction with the membrane. Mutants with a loss of IP$_4$ binding show reduced rasGAP activity suggesting that the PH domain of GAP1$^m$ binds both phospholipids and IP4 competitively to regulate the translocation and activity of GAP1$^m$.

GAP12 has a clearly defined expression pattern which, in contrast to other members of the GAP1 family, is highest in endocrine tissues. Mouse GAPIII was previously reported to be expressed primarily in the brain and in cultured neurons and oligodendrocytes prompting speculation that GAPIII may be involved in the ras mediated signaling pathways in myelinating cells. The range of expression for bovine p98GAP (96% identical to GAPIII) is also highest in brain cerebrum and cortex. Both proteins are expressed in spleen and lung at relatively lower levels, but there is no evidence of mRNA expression in the adrenal or thyroid glands. Expression of GAP1$^m$ is highest in brain, kidney and placenta with minimal expression in endocrine tissues. Therefore GAP12 is the first GAP1 family member to be strongly and selectively expressed in these tissue types.

In situ hybridization indicated that GAP12 mRNA is present in the follicular cells of the thyroid. These are the cells that secrete the thyroid hormones for storage in the thyroid follicles. The secretory activity of the follicular cells is controlled by thyroid stimulating hormone. In response to a secretory stimulus follicular cells engulf and release the thyroid hormones T3 and T4 into the bloodstream resulting in an increased rate of cellular metabolism and differentiation. GAP12 mRNA staining is strongest around those follicles whose colloid is more dense and counterstains more strongly. These may represent follicles within a ring of actively secreting follicular cells, which might be predicted to contain a greater concentration of hormones and thus counterstain more strongly. The adrenal gland consists of an outer cortex and an inner medulla which have a distinct embryonic origin and function. The adrenal cortex exhibits three concentric zones of cells producing different adrenal hormones. Cells of the zona glomerulus produce mineralocorticosteroids such as aldosterone, whereas cells of the zona fasiculata and zona reticularis produce glucocorticoid steroids. The cells of the adrenal medulla are modified post-ganglionic sympathetic neurones secreting catecholamines such as epinephrine and norepinephrine under the control of the autonomic nervous system. GAP12 mRNA is expressed within the medulla and zona glomerulus. Northern blot analysis also demonstrated GAP12 mRNA expression at a much lower level in the ovary and testis. The presence of GAP12 in these secretory glands suggests that it may be involved in the regulation of the secretory response.

Although the GRD of GAP12 is most similar to rasGAPs this study found no demonstrable elevation of the GTPase activity of H-ras (p21$^{ras}$) or related ras subfamily members, R-ras, TC21, rap1b, rap2a or ralA. Other members of the GAP1 family have been shown to elevate the rate of GTP hydrolysis of at least one of these small GTPases, although the specificity profiles of their GAP activity may differ. For example P98GAP shows a fivefold higher activity against R-Ras than H-ras, whereas GAP1$^m$ is more active against H-ras than R-ras. Another study reported that GAP1$^{IP4BP}$ demonstrated equivalent levels of GAP activity towards rap1a and H-ras, but GAP1$^m$ was shown not to stimulate the GTPase of rap1a. These results indicate that it is possible for related GAP1 family members to show differential substrate specificty. Therefore it is not unexpected that GAP12 does not stimulate the same GTPases as other GAP1 proteins.

There is a close association between mutations in ras and its regulators in the onset of human disorders. The GAP protein neurofibromin has been shown to play a role in tumor pathology, and for this reason GAP12 has the potential for involvement in human disease as a tumor suppresser. Chromosome 12 has been reported to harbor one or more tumor suppresser genes, since deletion of the q arm and loss of heterozygosity of chromosome 12 markers have been reported in various tumor types including gastrointestinal, pancreaticand germ cell. To investigate any role that GAP12 may play in human disease the gene was physically mapped to chromosome 12q23–24, enabling comparison with known disease linkages in this region. Many disease loci map to this region including Noonan syndrome, Darier disease and ulnar mammary syndrome, though none of these phenotypes reflect the expression pattern of GAP12 or would obviously be predicted to result from abnormalities in the control of ras mediated cell signaling.

In accordance with the subject invention, GAP12 genes are provided, which can serve many purposes. The GAP12 protein may be used in a screening for agonists and antagonists, and for assaying for the transcription of GAP12 mRNA. The protein or fragments thereof may be used to produce antibodies specific for the protein or specific epitopes of the protein. In addition, the gene may be employed for investigating endocrine tissue development, by screening fetal tissue, preparing transgenic animals to serve as models, and the like.

Examples 2

GAP12 Transgenic Knockout

The endogenous GAP12 gene of a mouse is "knocked-out" through the introduction of an alteration in the endogenous gene. A construct for generating the knockout mouse is made by replacing exon 43A4 (SEQ ID NO:3, position 458–552) with a neomycin cassette, or by replacing exon 1 with a neomycin cassette. The 43A4 exon contains the motifs essentialfor RasGAP activity, although the knockoutwill still encode the first 400 amino acids of the GAP12 protein.

A mouse genomic DNA phage library was screened with a mouse 5' musGAP cDNA probe. Three phage clones were recovered. From one phage clone, three fragments were subcloned into pBluescript KS (Stratagene); a 4.1 kb Xbal fragment, a 9.3 Kb Bam HI fragment and a 13.1 Kb EcoRI fragment. Each of these fragments contained exon 43A4, and were anchored at one end, since one of the terminal restriction sites in each fragment was provided by the pBluescript MCS.

Using PCR (with the EXTEND long range PCR kit from Boehringer Mannheim) on the 9 kB BamHI fragment with T3 and T7 primers from pBluescript and primers facing outwards from within the exon sequence, the 5' and 3' genomic sequence flanking the exon are being be amplified. The internal oligos carry "tails" providing appropriate restriction sites at one end of the PCR fragment. Restriction sites at the other ends of the PCR products are provided by sites in the pBluescript vector.

After cleavage the fragments are directionally cloned into the pPNT targeting vector (Tybulewicz et al. (1991) *Cell* 65:1153–1163) and electroporated into ES cells (RW4, Genome systems). NEO+ cells are selected for with G418 (Geneticin, Life techmologies) and cells in which the appropriate homologous recombination event has occurred are identified by Southern blot analysis using a probe derived from the 13.1 Kb EcoRI subclone.

Suitable ES cell clones are microinjected into 3.5 day old embryos, flushed from the oviducts of superovulated mice. Injected blastocysts are implanted into the uterus of pseudopregnant females. Chimeric mice are identified by coat color analysis and germline transmission identified by mating with C57BL/6 or FVB mice.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid encoding a mammalian GAP12 protein, wherein said GAP12 protein comprises the amino acid sequence as set forth in SEQ ID NO:2 or SEQ ID NO:4.

2. An isolated nucleic acid according to claim 1 wherein the nucleotide sequence of said nucleic acid is SEQ ID NO:1 or SEQ ID NO:3.

3. An isolated nucleic acid comprising at least 50 contiguous nucleotides of the sequence of SEQ ID NO:3.

4. An isolated nucleic acid that hybridizes under stringent conditions to the nucleic acid sequence of SEQ ID NO:3.

5. An expression cassette comprising a transcriptional initiation region, a nucleic acid encoding a mammalian GAP12 protein comprising the amino acid sequence as set forth in SEQ ID NO:2 or SEQ ID NO:4 and a transcriptional termination region.

6. A cell comprising an expression cassette according to claim 5 as part of an extrachromosomal element or integrated into the genome of a host cell as a result of introduction of said expression cassette into said host cell, and the cellular progeny of said host cell wherein said progeny maintain said expression cassette.

7. A method for producing mammalian GAP12 protein, said method comprising:

growing a cell according to claim 6, whereby said mammalian GAP12 protein is expressed; and isolating said GAP12 protein free of other proteins.

* * * * *